US007741957B2

(12) United States Patent
Wang et al.

(10) Patent No.: US 7,741,957 B2
(45) Date of Patent: Jun. 22, 2010

(54) METHOD FOR BREAK REMINDER AND DISPLAY DEVICE USING THE SAME

(75) Inventors: Wen-Wu Wang, Shenzhen (CN); Shih-Fang Wong, Tu-Cheng, Taipei Hsien (TW)

(73) Assignees: Hong Fu Jin Precision Industry (ShenZhen) Co., Ltd., Shenzhen, Guangdong Province (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 382 days.

(21) Appl. No.: 11/765,455

(22) Filed: Jun. 20, 2007

(65) Prior Publication Data

US 2007/0296556 A1 Dec. 27, 2007

(30) Foreign Application Priority Data

Jun. 23, 2006 (CN) ........................ 2006 1 0061314

(51) Int. Cl.
*G08B 1/00* (2006.01)
*G08B 23/00* (2006.01)
*A61B 3/02* (2006.01)
*A61B 5/117* (2006.01)

(52) U.S. Cl. .............................. 340/309.7; 340/309.16; 340/573.1; 340/573.7; 351/239; 600/594

(58) Field of Classification Search ....................... None
See application file for complete search history.

(56) References Cited

U.S. PATENT DOCUMENTS 5,305,238 A * 4/1994 Starr et al. .................. 702/176
5,888,173 A * 3/1999 Singhal ......................... 482/8
5,933,088 A * 8/1999 Lipp ......................... 340/7.52
6,592,223 B1 * 7/2003 Stern et al. .................. 351/239
7,233,312 B2 * 6/2007 Stern et al. .................. 345/156
7,481,779 B2 * 1/2009 Large ......................... 600/594
2002/0047828 A1 4/2002 Stern et al.
2004/0249872 A1 * 12/2004 Hsieh ......................... 708/200

FOREIGN PATENT DOCUMENTS

CN 2741060 11/2005
TW 449725 8/2001

* cited by examiner

*Primary Examiner*—Daniel Wu
*Assistant Examiner*—Fekadeselassie Girma
(74) *Attorney, Agent, or Firm*—Frank R. Niranjan

(57) ABSTRACT

The present invention provides method for break reminder and a display device. The display device includes a display unit; a clock counter; a distance estimator configured for detecting if the display device being used by a user, calculating distance between the user and a front of the display device, and generating a tracking signal if the distance is less than a predetermined distance; and a central processing unit configured for waiting for the tracking signal, resetting a worked time and a rested time when the tracking signal is received, signaling the clock counter to track the worked time, detecting if the worked time is less than a first predetermined time, and signaling the display unit to output the message prompt when the worked time is equal to or greater than the first predetermined time, thereby the present invention can prevent the user of the display device from fatigue.

10 Claims, 6 Drawing Sheets

METHOD FOR BREAK REMINDER AND DISPLAY DEVICE USING THE SAME

BACKGROUND OF THE INVENTION

1. Field of the Invention

The present invention relates to a method for preventing users from fatigue and display device using the same, and more particularly to method for break reminder and display device using the same.

2. Description of Related Art

In the information age, computers plays an ever increasing important role for work or for entertainment. Computers have become a hi-tech product that we need greatly in our daily lives.

However, according to a medical research, people generally develop heath problems from long-term computer usage. Amongst computer repetitive stress injuries (CRSI), some of the most common are the computer vision syndrome (CVS) and the carpal tunnel syndrome (CTS), these are caused by viewing a display device too long, typing on a keyboard over long time periods, and clutching and dragging a mouse over long periods. Generally speaking, computer users who use a computer continuously more than two hours per day have high risks in developing CVS. Reduced blinking frequency from concentrating on the screen too long causes moisture of the eyes to vaporize quickly and causes eye dryness, and may further induce chronic conjunctivitis and xerophthalmia. The flickering of the screen may also aggravate eyestrain even further, causing poor eyesight to get worse. The users may often be affected by eyestrain, headache, and fatigue. The CTS occurs from repeated physical movements that damages tendons, nerves, muscles, and other soft body tissues along the arms. The thousands of repeated keystrokes and clutching and dragging the mouse over long periods slowly damage the wrists and may cause numbness and pain.

Those who suffer from the CVS and the CTS should get proper medical therapy immediately, otherwise, they would suffer permanent injury and/or lasting pain. However, compared with the time and money spent for the therapy, the CVS and the CTS are far easier to prevent than to cure. Doctors suggest that computer users should shorten the time spent on the computer and take regular breaks to prevent CVS and CTS.

Therefore, a heretofore unaddressed need exists in the industry to prevent the users of the display device from fatigue.

SUMMARY OF THE INVENTION

The present invention provides a method for break reminder and a display device using the same. The display device tracks a worked time when the display device detects that the user is within a predetermined distance from a front of the display device, and outputs a message prompt to alert the user to take a rest when the worked time is equal to or greater than a predetermined time. Thereby, the present invention can prevent users of the display device from fatigue.

The display device includes a display unit, a clock counter, a distance estimator and a central processing unit. The display unit is configured for outputting data including a message prompt. The clock counter is configured for tracking a worked time and a rested time. The distance estimator detects if the display device is being used by a user, calculates a distance between the user and a front of the display device, compares the distance with a predetermined distance, and generates a tracking signal if the distance is equal to or less than the predetermined distance. The central processing unit includes an initialization module for waiting for the tracking signal, resetting the worked time and the rested time if the tracking signal is received; and a work detection module for signaling the clock counter to track the worked time, comparing the worked time with a first predetermined time, and signaling the display unit to display the message prompt if the worked time is equal to or greater than the first predetermined time.

Other systems, methods, features, and advantages will be or become apparent to one with skill in the art upon examination of the following drawings and detailed description. It is intended that all such additional systems, methods, features, and advantages be included within this description, be within the scope of the present invention, and be protected by the accompanying claims.

DETAILED DESCRIPTION OF THE INVENTION

A break reminder can be adopted in a liquid crystal display (LCD), an electronic book (E-book), a TV set, and so on. In the following embodiments, for simplicity, the function incorporated in an LCD is depicted. The following detailed description of preferred embodiments is made with reference to the attached drawings.

Figure 1:
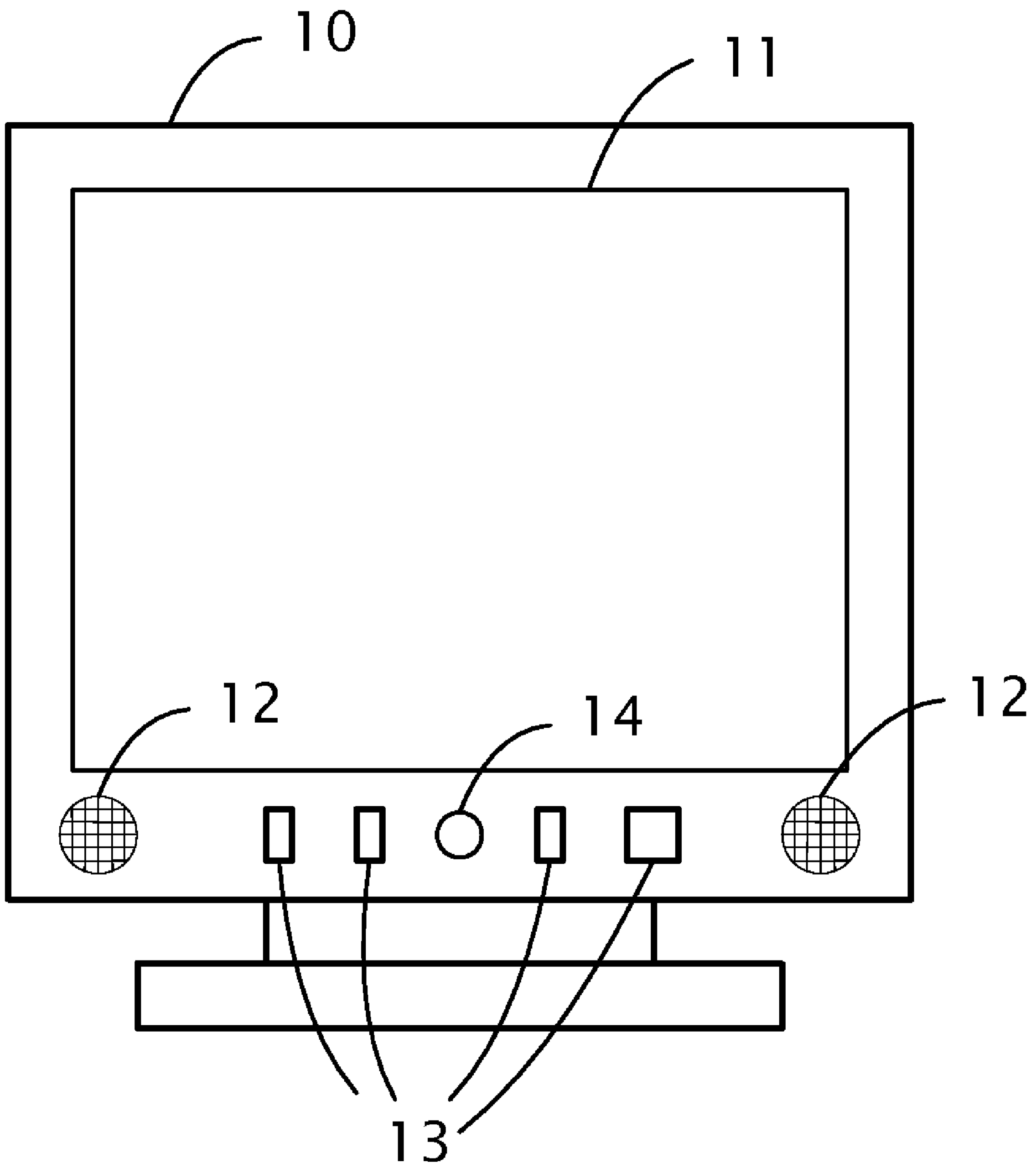
FIG. 1 is a front view of a display device in accordance with a preferred embodiment of the present invention.

FIG. 1 is a schematic diagram of an LCD 10 in accordance with a preferred embodiment of the present invention. The LCD 10 includes a display panel 11, a speaker 12, keys 13, and a distance estimator 14. The display panel 11 is configured for displaying message prompts. The speakers 12 are configured for reproducing sounds. The keys 13 is configured for powering on/off the LCD 10, adjusting parameters of an on-screen display (OSD) of the LCD 10 in response to operational inputs. The distance estimator 14 is configured for detecting if a user is within a predetermined distance, such as sixty centimeters from the LCD 10. The predetermined distance is an average distance between the user and a front of the LCD 10 when the user is using the LCD 10. If it is detected that the user is within the predetermined distance, it means that the user is using the LCD 10. The distance estimator 14 can be an infrared ray (IR) distance meter, an ultrasonic distance meter, and the like.

Figure 2:
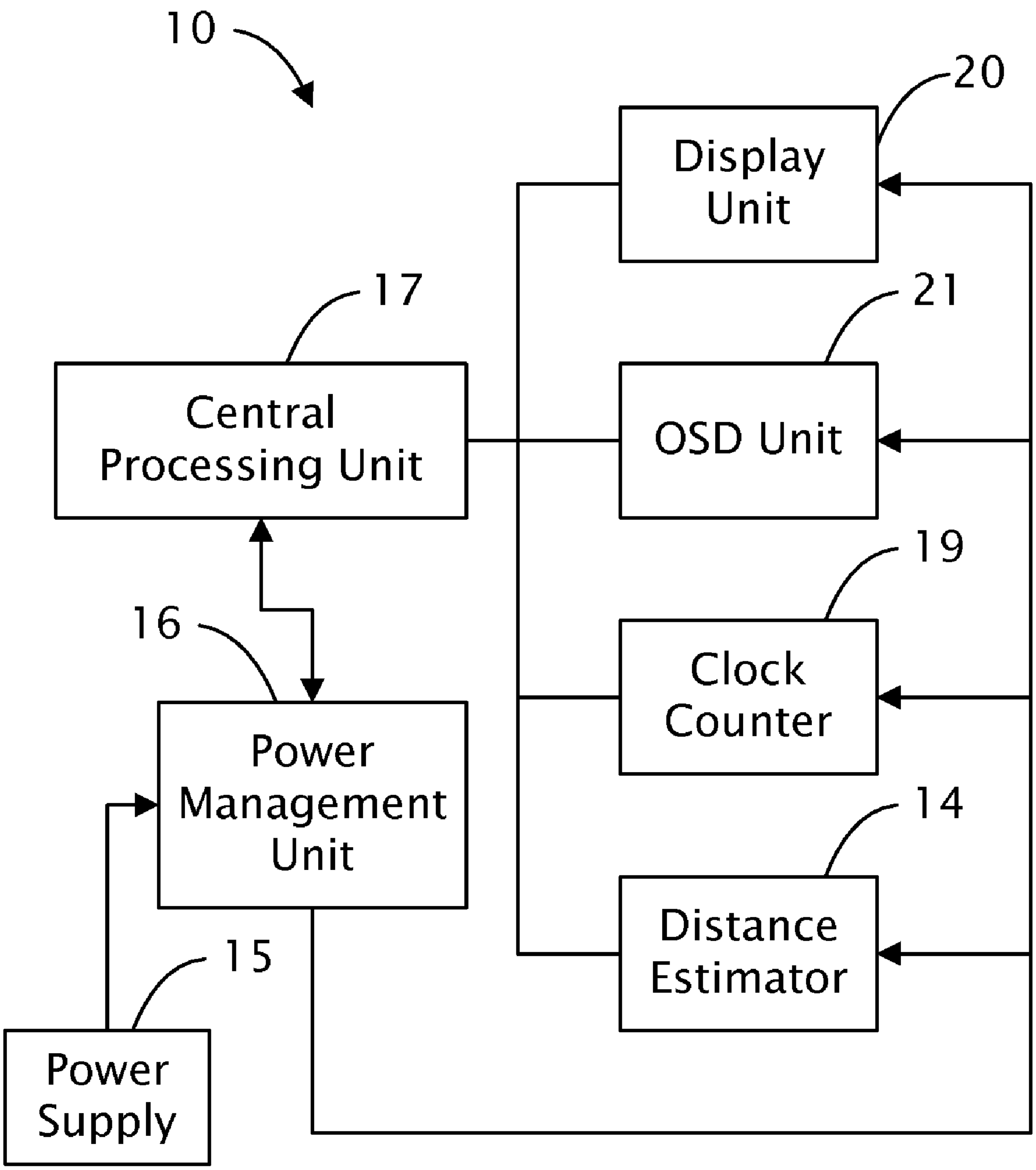
FIG. 2 is a block diagram of a hardware infrastructure of the display device of FIG. 1.

FIG. 2 is a block diagram of a hardware infrastructure of the LCD 10 of FIG. 1. The LCD 10 includes a distance estimator 14, a power supply 15, a power management unit 16, a central processing unit (CPU) 17, a clock counter 19, a display unit 20, and an OSD unit 21.

The power supply 15 is configured for connecting to the LCD 10, and providing voltage to the LCD 10. The power management unit 16 transforms the voltage to corresponding work voltage of components of the LCD 10, and provides the work voltage to the corresponding components of the LCD 10. The components include the CPU 17, the display unit 20 and the OSD unit 21.

The OSD unit 21 includes a plurality of parameters of the LCD 10 such as chrominance and luminance. The CPU 17 controls the display unit 20 to output data to the display panel 11. The display panel 11 displays the data including a message prompt.

The clock counter 19 is configured for tracking a worked time and a rested time. The worked time represents a time period when the user is within the predetermined distance from the LCD 10. The rested time represents a time period when the user is not detected to be within the predetermined distance from the LCD 10.

If it is detected that the user is within a predetermined distance in front of the LCD 10, the distance estimator 14 generates a tracking signal, and sends the tracking signal to the CPU 17.

Figure 3:
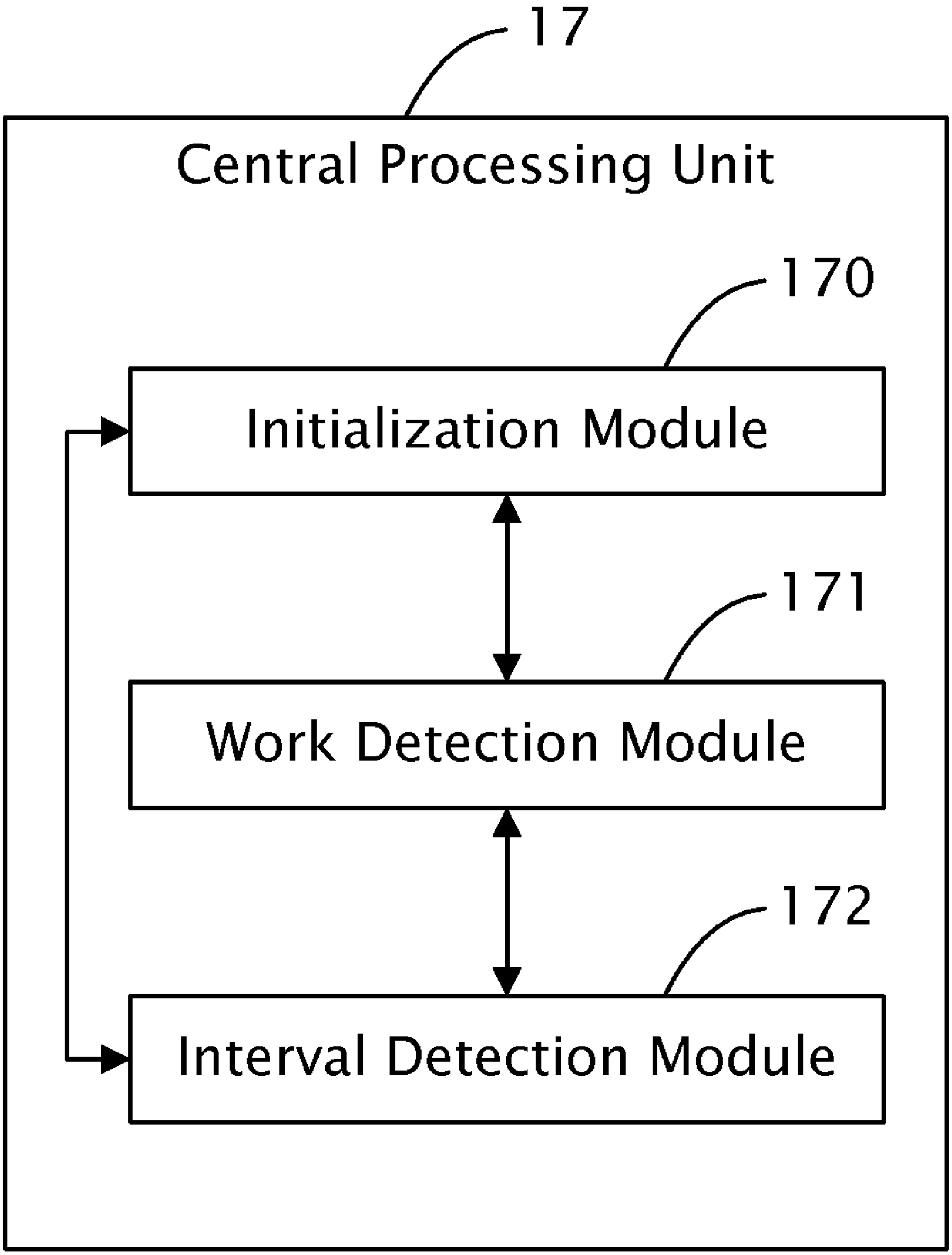
FIG. 3 is a schematic diagram of main function modules of a central processing unit of FIG. 2.

Referring to FIG. 3, the CPU 17 includes an initialization module 170, a work detection module 171, and an interval detection module 172. The initialization module 170 waits for the tracking signal, resets the worked time, and the rested time if the tracking signal has been received.

The work detection module 171 signals the clock counter 19 to track the worked time, detects if the worked time is equal to or greater than a first predetermined time, and signals the display unit 20 to output the message prompt to the display panel 11 if the worked time is equal to or greater than the first predetermined time. The message prompt is used for alerting the user to take a rest, and may have a message such as "It is time to take a rest." The first predetermined time presents a time period when the user is working, a time such as an hour.

After the work detection module 171 signals the display unit 20 to output the message prompt, the interval detection module 172 signals the clock counter 19 to track the rested time, and detects if the rested time is equal to or greater than a second predetermined time. If the rested time is equal to or greater than the second predetermined time, the interval detection module 172 signals the display unit 20 to terminate the message prompt. The second predetermined time represents a time period that the user needs to rest after working the first predetermined time, a time such as 10 minutes.

Figure 4:
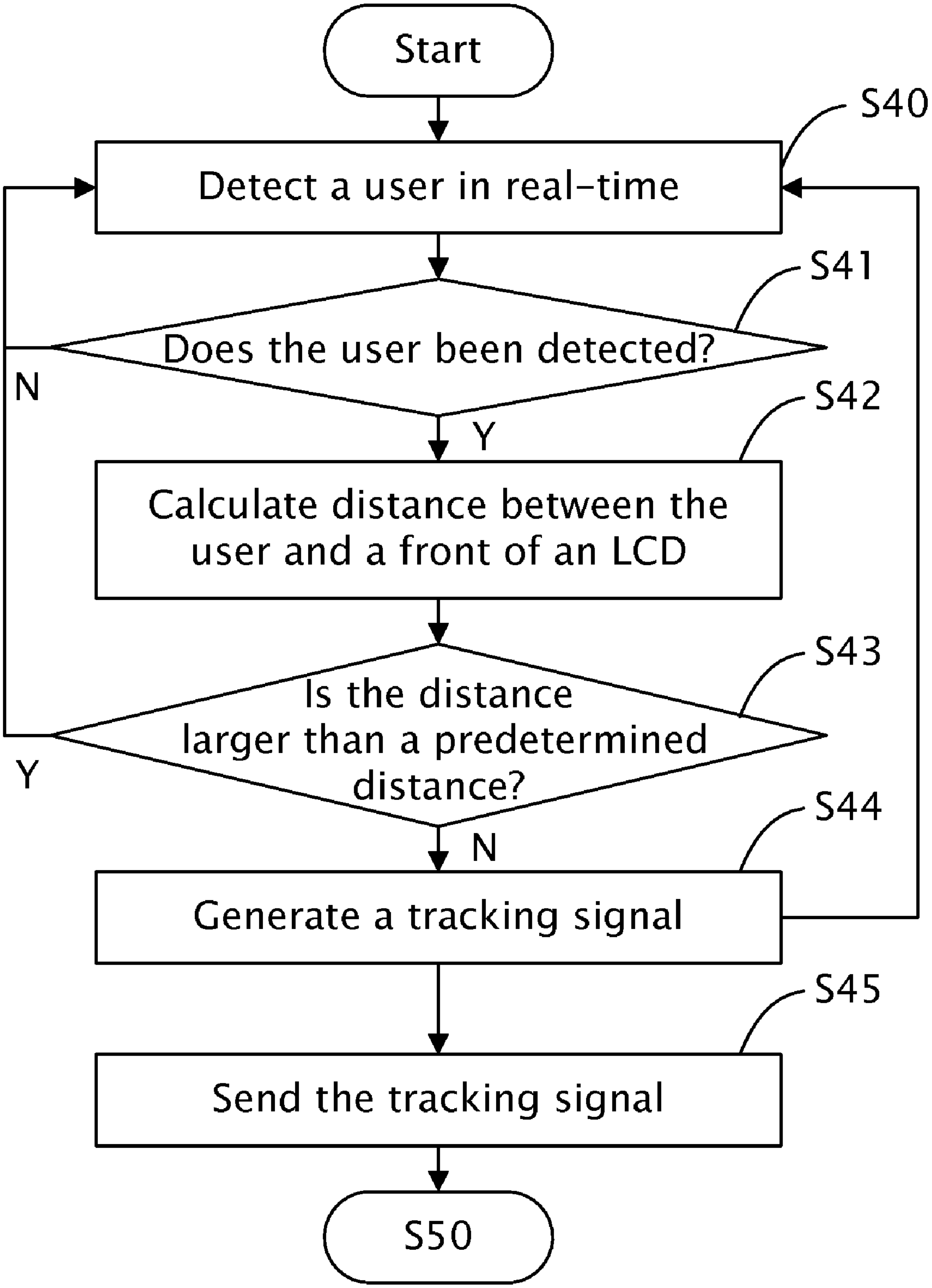
FIGS. 4-6 are flowcharts of a preferred method of preventing the users of the LCD from fatigue.
Figure 5:
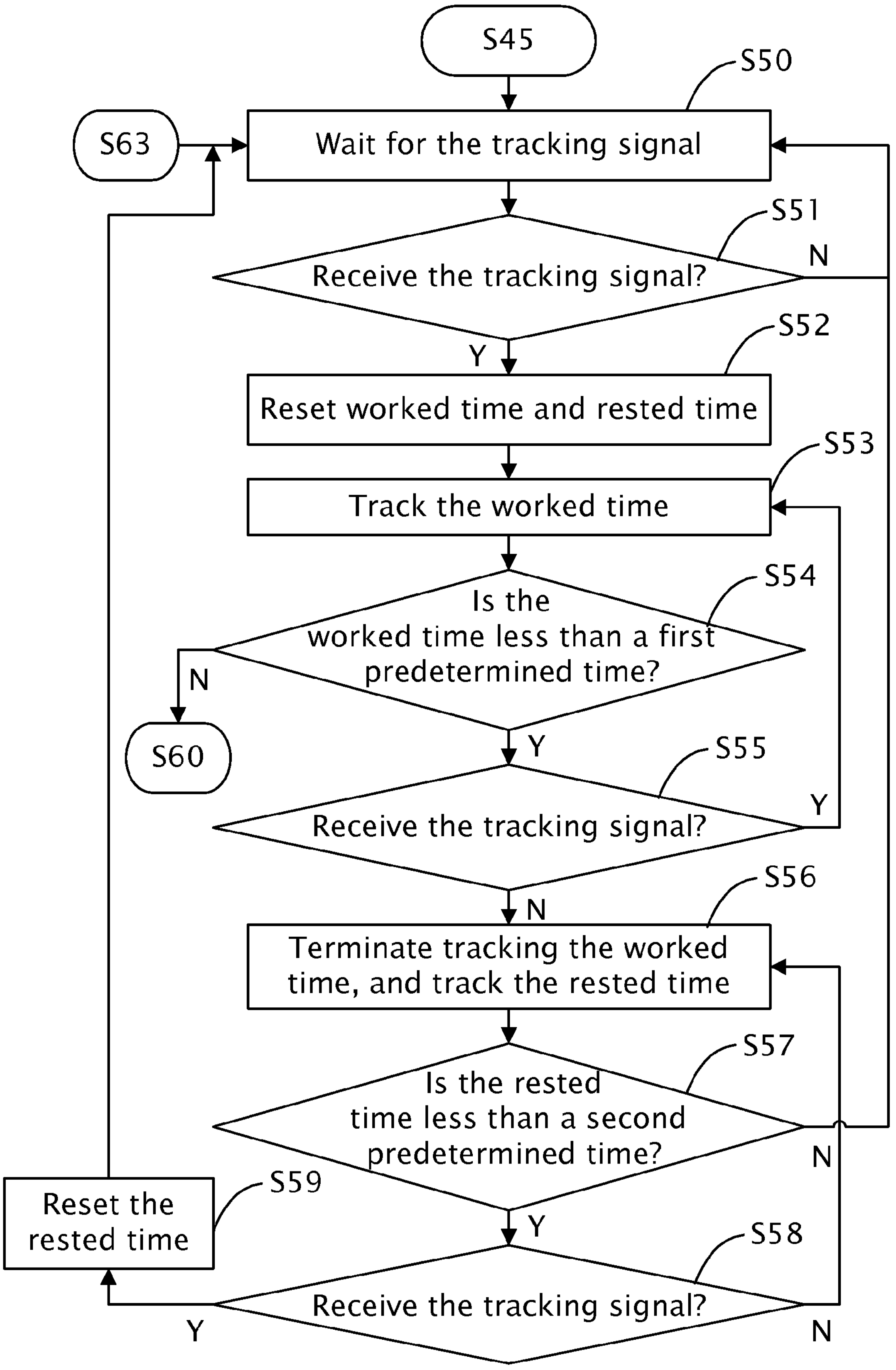
Figure 6:
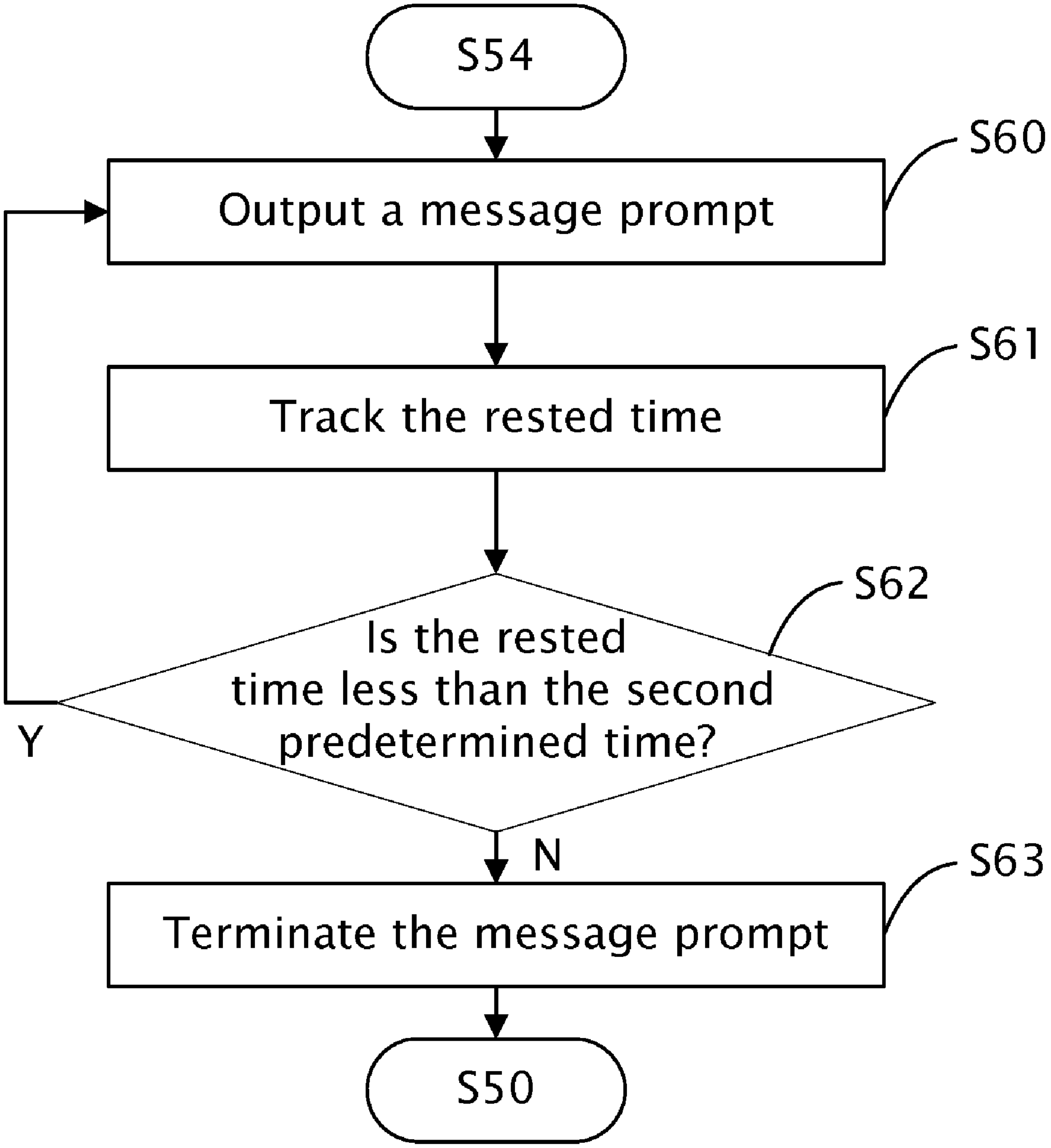

FIGS. 4-6 are flowcharts of a preferred method for preventing the users of the LCD 10 from fatigue. Referring to FIG. 4, in step S40, the distance estimator 14 detects the user within the predetermined area in front of the LCD 10 in real-time.

In step S41, the distance estimator 14 determines if the user is detected.

If the distance estimator 14 has not detected the user, the procedure goes to step S40. If the distance estimator 14 detects the user, the procedure goes to step S42, in step S42 the distance estimator 14 calculates the distance between the user and the front of the LCD 10.

In step S43, the distance estimator 14 compares the calculated distance with the predetermined distance, and determines if the distance is larger than the predetermined distance.

If the distance estimator 14 determines that the distance is larger than the predetermined distance, the procedure goes back to step S40. If the distance estimator 14 determines that the user is equal to or less than the predetermined distance, the procedure goes to step S44, in step S44, the distance estimator 14 generates the tracking signal.

In step S45, the distance estimator 14 sends the tracking signal to the CPU 17.

Referring to FIG. 5, in step S50, the initialization module 170 of the CPU 17 waits for the tracking signal.

In step S51, the initialization module 170 detects if the tracking signal has been received from the distance estimator 14.

If the initialization module 170 has not received the tracking signal, the procedure goes to step S50. If the initialization module 170 receives the tracking signal, in step S52, the initialization module 171 resets the worked time and the rested time.

In step S53, the initialization module 170 signals the clock counter 19 to track the worked time.

In step S54, the work detection module 171 compares the worked time with the first predetermined time, and detects if the worked time is less than the first predetermined time.

If the worked time is less than the first predetermined time, in step S55, the initialization module 170 detects if the tracking signal has been received from the distance estimator 14.

If the initialization module 170 receives the tracking signal from the distance estimator 14, the procedure goes to step S53. If the initialization module 170 has not received the tracking signal from the distance estimator 14, in step S56, the initialization module 170 signals the clock counter 19 to terminate tracking the worked time, and start to track the rested time.

In step S57, the interval detection module 172 compares the rested time with the second predetermined time, and detects if the rested time is less than the second predetermined time.

If the rested time is equal to or greater than the second predetermined time, the procedure goes to step S50. If the rested time is less than the second predetermined time, in step S58, the initialization module 170 detects if the tracking signal has been received.

If the initialization module 170 has not received the tracking signal, the procedure goes to step S56. If the initialization module 170 receives the tracking signal, in step S59, the initialization module 170 resets the rested time, and the procedure goes to step S50.

Referring to FIG. 6, in step S54, if the worked time is equal to or greater than the first predetermined time, in step S60, the initialization module 170 signals the display unit 20 to output the message prompt to the display panel 11.

After the initialization module 170 signals the display unit 20 to output the message prompt, in step S61, the interval detection module 172 signals the clock counter 19 to track the rested time.

In step S62, the interval detection module 172 compares the rested time with the second predetermined time, and detects if the rested time is less than the second predetermined time.

If the rested time is less than the second predetermined time, the procedure goes to step S60. If the rested time is equal to or greater than the second predetermined time, the interval detection module 172 signals the display unit 20 to terminate the message prompt, and the procedure goes to step S50.

It is understood that the invention may be embodied in other forms without departing from the spirit thereof. Thus, the present examples and embodiments are to be considered in all respects as illustrative and not restrictive, and the invention is not to be limited to the details aforementioned.

What is claimed is:

1. A display device for break reminder, the display device comprising: a display unit being configured for outputting data comprising a message prompt;

a clock counter being configured for tracking a worked time and a rested time;

a distance estimator being configured for detecting if the display device is being used by a user, calculating a distance between the user and a front of the display device, comparing the distance with a predetermined distance, and generating a tracking signal if the distance is equal to or less than the predetermined distance; and a central processing unit comprising:

an initialization module for waiting for the tracking signal, resetting the worked time and the rested time if the tracking signal is received; and a work detection module for signaling the clock counter to track the worked time, comparing the worked time with a first predetermined time, and signaling the display unit to display the message prompt if the worked time is equal to or greater than the first predetermined time;

wherein if the worked time is less than the first predetermined time and the initialization module has not received the tracking signal, the interval detection module signals the clock counter to terminate tracking the worked time and track the rested time, detects if the rested time is equal to or greater than the second predetermined time; if the rested time is equal to or greater than the second predetermined time, the interval detection module waits for the tracking signal.

2. The display device according to claim 1, wherein the central processing unit further comprises an interval detection module for signaling the clock counter to track the rested time after the work detection module signals the display unit to output the message prompt, detecting if the rested time is equal to or greater than a second predetermined time, and signaling the display unit to terminate the message prompt if the rested time is equal to or greater than the second predetermined time.

3. The display device according to claim 1, wherein if the worked time is less than the first predetermined time and the initialization module receives the tracking signal, the clock counter tracks the worked time.

4. The apparatus according to claim 1, wherein when the rested time is less than the second predetermined time and the initialization module has not received the tracking signal, the clock counter track the rested time.

5. The apparatus according to claim 1, wherein if the rested time is less than the second predetermined time and the initialization module receives the tracking signal, the interval detection module waits for the tracking signal.

6. A method for break reminder, the method comprising the steps of:

detecting if the display device is being used by the user in real-time;

calculating a distance between the user and a front of the display device after the user is detected;

comparing the distance with a predetermined distance;

determining if the distance is equal to or less than the predetermined distance;

generating a tracking signal if the distance is equal to or less than the predetermined distance;

waiting for the tracking signal;

resetting a worked time and a rested time if the tracking signal is received;

tracking the worked time;

detecting if the worked time is equal to or greater than a first predetermined time; and outputting the message prompt when the worked time is equal to or greater than the first predetermined time;

terminating tracking the worked time if the worked time is less than the first predetermined time and the tracking signal has not been received;

tracking the rested time detecting if the rested time is equal to or greater than a second predetermined time;

resetting the worked time and the rested time if the rested time is equal to or greater than the second predetermined time; and waiting for the tracking signal.

7. The method according to claim 6, further comprising the steps of:

waiting for the rested time after outputting the message prompt;

detecting if the rested time is equal to or greater than a second predetermined time; and terminating the message prompt if the rested time is equal to or greater than the second predetermined time.

8. The method according to claim 6, further comprising the step of: if the worked time is less than the first predetermined time and the tracking signal is received, continue tracking the worked time.

9. The method according to claim 7, further comprising the step of: if the rested time is less than the second predetermined time and the tracking signal has not been received, continuing tracking the rested time.

10. The method according to claim 7, further comprising the steps of: if the rested time is less than the second predetermined time and the tracking signal is received, resetting the rested time and waiting for the tracking signal.

* * * * *